United States Patent [19]

Obenour

[11] 4,341,216

[45] Jul. 27, 1982

[54] BREATHABLE BACKSHEET FOR DISPOSABLE DIAPERS

[75] Inventor: Mary C. Obenour, Fairfield, Ohio

[73] Assignee: The Procter & Gamble Company, Cincinnati, Ohio

[21] Appl. No.: 239,090

[22] Filed: Feb. 27, 1981

[51] Int. Cl.³ ............................................. A41B 13/02
[52] U.S. Cl. .................................................. 128/287
[58] Field of Search ........... 128/284, 286, 287, 290 R, 128/DIG. 30

[56] References Cited

U.S. PATENT DOCUMENTS

| | | |
|---|---|---|
| 2,068,997 | 1/1937 | Spanel . |
| 2,068,998 | 1/1937 | Spanel . |
| 2,544,069 | 3/1951 | Cutler . |
| 2,604,097 | 7/1952 | White ................................. 128/287 |
| 3,156,242 | 11/1964 | Crowe, Jr. . |
| 3,881,489 | 5/1975 | Hartwell . |
| 3,989,867 | 11/1976 | Sisson . |
| 4,306,559 | 12/1981 | Nishizawa et al. ................. 128/287 |

Primary Examiner—C. Fred Rosenbaum
Attorney, Agent, or Firm—Monte D. Witte; Richard C. Witte; Fredrick H. Braun

[57] ABSTRACT

Disposable diapers provided with a two-element breathable backsheet. The two elements are a vapor pervious, relatively liquid impervious outer sheet and a liquid impervious inner panel. An absorbent core is the third necessary element of the disposable diaper. The inner panel is placed between the outer sheet and the absorbent core in the crotch region of the disposable diaper. There is no requirement that the inner panel be affixed to the outer sheet in any manner other than to insure the maintenance of their relative orientations during use. The disposable diaper can be provided with an optional topsheet disposed on the absorbent core on the side opposite the breathable backsheet.

17 Claims, 6 Drawing Figures

BREATHABLE BACKSHEET FOR DISPOSABLE DIAPERS

BACKGROUND OF THE INVENTION

1. Field of the Invention

This invention concerns generally absorptive devices such as disposable diapers and, more particularly, a backing for such devices which retards the passage of liquids while permitting the passage of vapors.

BACKGROUND ART

Absorptive devices such as diapers are well known for their use in absorbing and retaining liquid discharges from the human body. Diapers can be either of the more or less permanent type which are intended to be cleaned and reused a number of times or of the disposable type which are intended to be used only once and then discarded. It is known that the exterior of diapers, particularly of disposable diapers, can be covered with a flexible, impermeable sheet to prevent any absorbed liquid from passing through the diaper and soiling adjacent articles such as clothing, bedding, and the like. These covering sheets are known as backsheets and are generally constructed from a waterproof plastic such as polyethylene. The backsheets do prevent liquid from passing therethrough and do help contain liquid within the diaper. Unfortunately, they also sometimes make the diaper feel hot and uncomfortable to wear because of their total impermeability. In addition, their impermeability precludes self-drying of the diaper which would otherwise occur through evaporation of the liquid contained therein.

Backsheets which are pervious to vapor are known as breathable backsheets and have been described in the art. These breathable backsheets provide a cooler garment and permit some drying of the diaper while it is being worn. In general, these breathable backsheets are intended to allow the passage of vapor through them while retarding the passage of liquid.

For example, U.S. Pat. No. 3,156,242 issued to Crowe, Jr. on Nov. 10, 1964 teaches the use of a microporous film as a breathable backsheet. U.S. Pat. No. 3,881,489, issued to Hartwell on May 6, 1975, teaches a breathable backsheet comprising in combination two layers, the first of which is a low void volume perforated thermoplastic film and the second of which is a porous high void volume hydrophobic tissue. U.S. Pat. No. 3,989,867 issued to Sisson on Nov. 2, 1976 teaches a breathable backsheet provided with tapered hollowed bosses which prevent the passage of liquids while allowing vapors to pass readily therethrough.

While these backsheets do provide some measure of improvement over the more common impermeable backsheets, and while the last two named devices are of particular value, devices providing for the more efficient passage of vapor while still restricting the passage of liquid when subjected to the pressure encountered during normal wearing have still been sought.

SUMMARY OF THE INVENTION

In accordance with the present invention there is provided a diaper comprising an absorbent core and a vapor pervious, liquid impervious (breathable) backsheet wherein the breathable backsheet comprises two elements: an outer sheet and an inner panel. The outer sheet is so constructed as to be vapor pervious and relatively liquid impervious in a central region extending longitudinally along the length of the sheet from the front waist region to the rear waist region of the diaper and impermeable in the two longitudinal regions adjacent to and lying on either side of the central region. The inner panel is an impermeable sheet extending substantially completely laterally across the width of the outer sheet in the crotch region of the diaper, but extending only a fraction of the distance longitudinally along the length of the outer sheet in the crotch region. The two elements are superimposed to form a backsheet.

Accordingly, it is an object of the present invention to provide a disposable diaper which allows the passage of vapor thereby providing cooling and drying effects to the disposable diaper, but which retains liquid within the disposable diaper.

BRIEF DESCRIPTION OF THE DRAWINGS

While the specification concludes with claims particularly pointing out and distinctly claiming the subject matter which is regarded as forming the present invention, it is believed that the invention will be better understood from the detailed description appearing in the following section taken in conjunction with the accompanying drawings, in which the thicknesses of some of the materials are exagerated for clarity and in which:

DETAILED DESCRIPTION OF THE INVENTION

The absorptive devices of this invention, and more particularly the disposable diapers of this invention, comprise two necessary parts: an absorbent core and a backsheet as hereinafter described. Optionally, and preferably, a topsheet is provided as a third part. The topsheet, of course, is an element which is designed to be interposed between the absorbent core of the diaper and the body of the wearer. The following description of the invention includes the optional topsheet.

Figure 1:
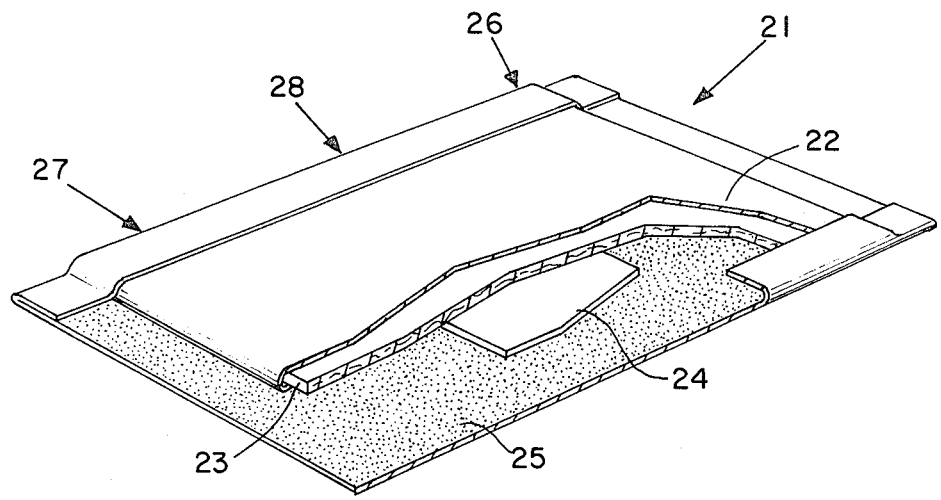
FIG. 1 is a perspective view of one embodiment of a diaper of this invention in an unfolded condition and having various layers cut away.

Referring now to the drawings and in particular to FIG. 1 thereof, disposable diaper 21 is one preferred construction of the disposable diaper of the present invention. Diaper 21 is fabricated from multiple plies of various materials. The preferred construction illustrated in FIG. 1 includes topsheet 22, absorbent core 23, inner panel 24, and outer sheet 25.

Unless otherwise indicated hereinafter, the use of the term "backsheet" will denote the backsheet of this invention which comprises an inner panel and an outer sheet as hereinafter defined.

Inner panel 24 is superimposed on outer sheet 25 to form the backsheet. Absorbent core 23 is superimposed on inner panel 24 and outer sheet 25; topsheet 22 is superimposed on absorbent core 23. Disposable diaper 21 will have a front waist area 26, a rear waist area 27, and a crotch area 28. When disposable diaper 21 is worn, front waist area 26 is generally placed adjacent the waist of the wearer at the front of the wearer's body while rear waist area 27 is generally placed adjacent the waist of the wearer at the rear of the wearer's body. Crotch area 28 is generally placed adjacent the wearer's crotch area. In certain constructional configurations, front waist area 26 and rear waist area 27 are interchangeable; that situation prevails in the embodiment shown in FIG. 1.

Disposable diaper 21 can be considered to be divided into two portions by an imaginary longitudinal center line running generally from front waist area 26 to rear waist area 27. Disposable diaper 21 can also be considered to be divided into two portions by an imaginary lateral center line running generally across the area through crotch region 28. (It should be noted that the embodiment illustrated in FIG. 1 is symmetrical about the two imaginary center lines, but other embodiments need not be so symmetrical.)

As noted, absorbent core 23 is superimposed over inner panel 24 and outer sheet 25 and topsheet 22 is superimposed over absorbent core 23. Topsheet 22 can be longer in the longitudinal dimension than absorbent core 23 and so that it can be folded around and under the longitudinal ends of absorbent core 23 as shown in FIG. 1. The combination of topsheet 22 and absorbent core 23 is superimposed on outer sheet 25 so that lateral edges and longitudinal ends are generally adjacent and parallel.

Topsheet 22 can be any compliant, soft feeling, porous paper or nonwoven fabric web. Examples of suitable topsheets are described in U.S. Pat. No. Re. 26,151 issued to Duncan et al. on Jan. 31, 1967, which patent is herein incorporated by reference. The particular topsheet suggested by Duncan et al. is a hydrophobic nonwoven rayon web bonded with a thermoplastic binder. Other suitable topsheets are shown in U.S. Pat. No. 3,860,003 issued to Buell on Jan. 14, 1975, which patent is herein incorporated by reference. An especially preferred topsheet is a spunbonded nonwoven polyester fabric made from fibers of from about 2.2 to about 2.5 denier and having a basis weight of about 17 grams per square meter.

Absorbent core 23 can be formed from any of the materials well known to those of ordinary skill in the diaper art. Suitable examples include multiple plies of creped cellulose wadding, fluffed cellulose fibers or wood pulp fibers sometimes known as airfelt, and textile fibers. The absorbent core can be semi-rigid as described in the Buell patent. A preferred absorbent core is formed from airlaid comminution grade wood pulp as is well known to those skilled in the art. A basis weight of from about 0.02 to about 0.04 gram per square centimeter is preferred.

The backsheet of this invention is a combination comprising two elements, inner panel 24 and outer sheet 25.

Figure 4:
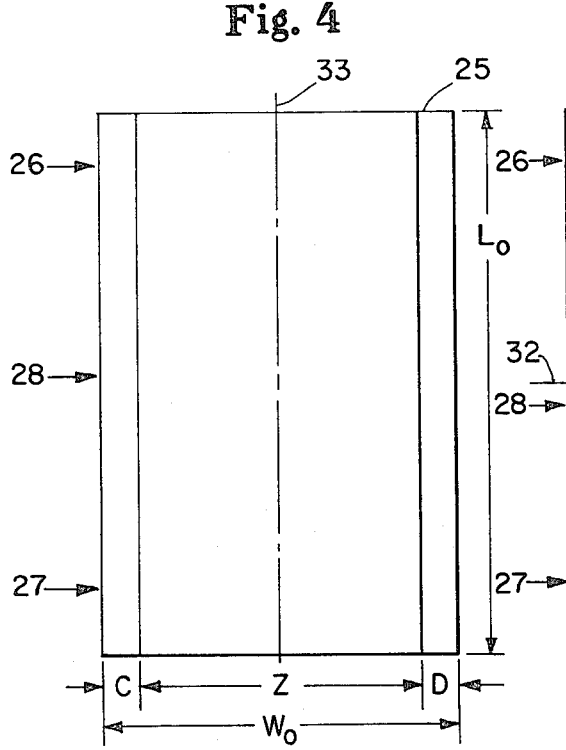
FIG. 4 is a representational plan view of the outer sheet of this invention showing the various regions thereof.

Outer sheet 25 is shown in representational plan view in FIG. 4. Outer sheet 25 is provided with regions of two types: impermeable and vapor pervious, relatively liquid impervious. Impermeable regions will permit essentially no transport of liquid or vapor therethrough. Vapor pervious, relatively liquid impervious regions will have a vapor transfer rate greater than about 0.6 gram per 100 square centimeters per hour and will allow liquid to pass therethrough at a liquid transfer rate of less than about 5%.

Liquid transfer rate as used herein is a measure of the liquid barrier properties of a relatively liquid impervious material.

The sample to be evaluated is placed between a wetted standard core and a fluid collection device. The wetted standard core is subjected to uniform pressure in such a manner that any liquid expelled from the wetted standard core must pass through the sample into the fluid collection device. Naturally, if the sample is impermeable, no liquid will pass through it. The more liquid which passes through the sample, the less liquid impervious is the sample.

The standard core is formed from airlaid comminution grade wood pulp and has a basis weight of 0.023 gram per square centimeter. It is covered by a tissue (as hereinafter described) and is in the form of a circle 7.5 centimeters in diameter. It is wetted with five times its weight of a synthetic urine which is distilled water the surface tension of which has been reduced to 45 dynes per centimeter by the addition of a nonionic surfactant (such as Triton X-100 made by Rohm and Haas Company of Philadelphia, PA.) and which also contains 1% by weight sodium chloride.

The fluid collection device comprises two plies of Whatmann #4 Laboratory Filter Paper, each 12.7 centimeters in diameter.

The sample, wetted core, and fluid collection device are subjected to a 3,078 gram weight uniformly distributed across the surface of the wetted standard core. At the end of 5 minutes, the weight is removed, the test assembly is disassembled, and the amount of liquid in the fluid collection device is measured by weighing. The liquid transfer rate is defined as the amount of liquid, in terms of percent of liquid originally present in the wetted standard core, which passes through the sample into the fluid collection device during the five minute test period.

Vapor transfer rate is measured by a similar technique. The standard core mentioned above is placed on an impervious support and is wetted with five times its weight of the synthetic urine described above. The sample to be evaluated is firmly stretched across the core in such an orientation as it would have when used in a disposable diaper of this invention. The whole assembly is placed in a 23° C., 50% relative humidity atmosphere for one hour. The amount of liquid which evaporates from the core is determined by weighing. The vapor transfer rate is defined as the amount of liquid evaporated and is expressed in grams of liquid per 100 square centimeters of sample per hour.

In outer sheet 25, the vapor pervious, relatively liquid impervious region is a central region extending longitudinally along imaginary longitudinal center line 33 as shown in FIG. 4. The regions extending longitudinally adjacent to and lying on either side of the immediately hereinbefore described central region are impermeable to both liquid and vapor. In FIG. 4, the vapor pervious, relatively liquid impervious region is indicated generally by Z while the impermeable regions are indicated generally by C and D. (Reference letters are used at this point in the discussion to refer generally to specific areas of outer sheet 25; they will be used later in this discussion as measurements in the description of the relative sizes of the impermeable and the vapor pervious, relatively liquid impervious regions.) The width of outer sheet 25 is shown by $W_O$ and its length by $L_O$.

The outer sheet can be constructed of any suitable material and in any suitable manner so long as the respective regions are impermeable and vapor pervious, relatively liquid impervious.

One material which has been found suitable for the outer sheet is a thermoplastic film (such as common polyethylene film) which has been perforated in any convenient manner. A preferred degree of perforation can be described in terms of a dimensionless R value which is defined as $$R = \frac{d\,(OA)}{c}$$

wherein d is the average diameter, in centimeters, of the perforations in the film; OA is the total open area of the perforated film, expressed as a percentage; and c is the average caliper (or length) of the perforations. Normally, when apertures are formed in a thermoplastic film, they take the form of somewhat irregular cones open at both apex and base. Average diameter is the arithmetic average of the diameter of the cones so formed. Pore caliper is the average height of the cones so formed. (Of course, if the apertures should be uniformly cut from the film without the normal formation of the cones, c will be film thickness.)

A perforated film having an R value between about 2 and about 40, preferably between about 5 and about 25, usually has the proper liquid transfer rate and vapor transfer rate for use in the present invention.

Figure 2:
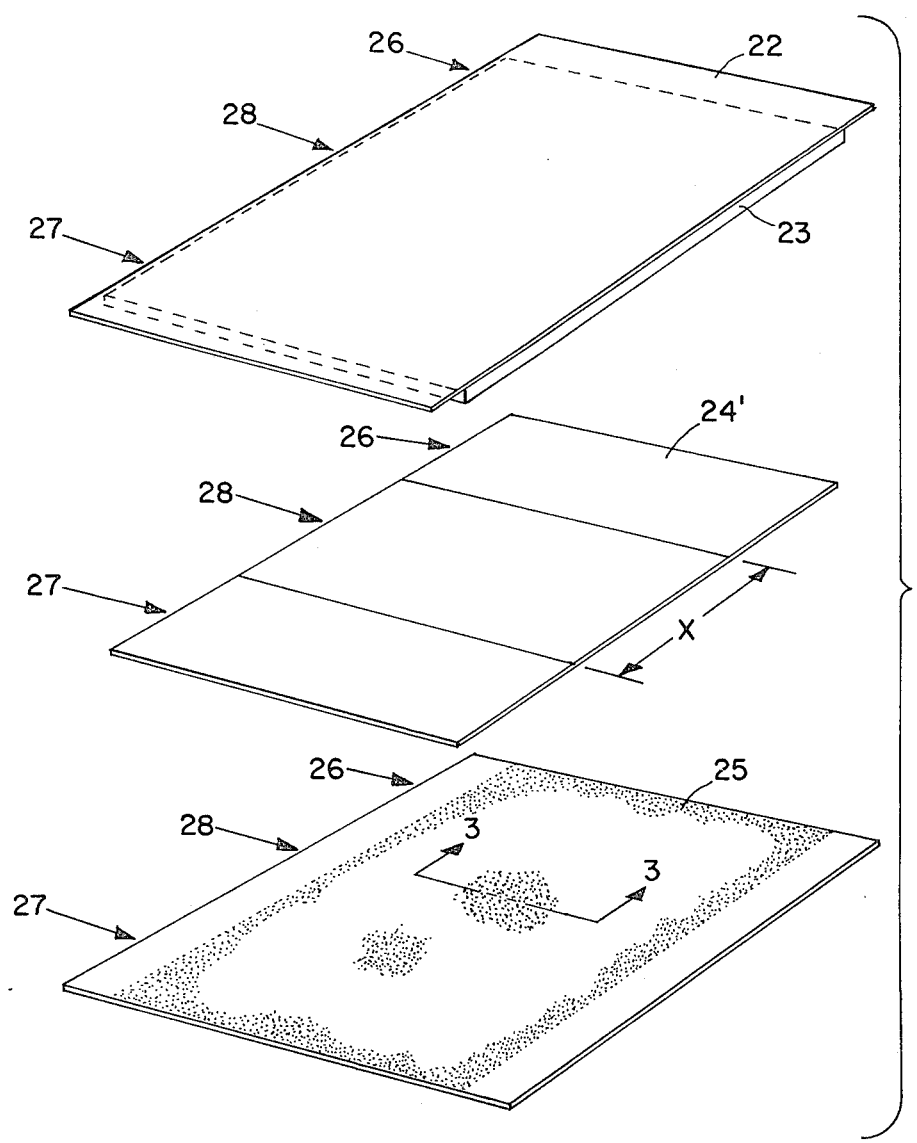
FIG. 2 is an exploded perspective view of another embodiment of a diaper of this invention showing the manner in which the various components are superimposed.
Figure 3:
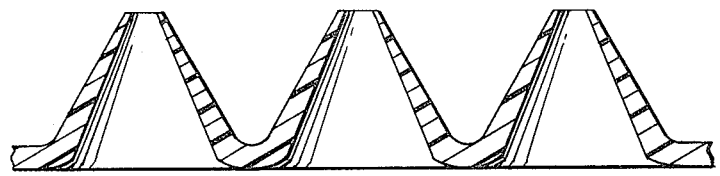
FIG. 3 is a cross section taken along line 3—3 of FIG. 2.

Another construction of outer sheet 25 utilizes the tapered capillaries described in U.S. Pat. No. 3,929,135, issued to Thompson on Dec. 30, 1975, which patent is herein incorporated by reference. This patent describes an absorptive device having as one element an unidirectionally liquid impervious sheet provided with tapered capillaries of critical dimensions. This element described by Thompson can be used as the basis for outer sheet 25. That is to say, outer sheet 25 can be provided with tapered capillaries, as taught by Thompson, in the vapor pervious, relative liquid impervious region Z. Outer sheet 25, in this embodiment, can be any suitable impermeable material, such as low density polyethylene, of from about 0.013 to about 0.076 millimeter, preferably about 0.020 to about 0.030 millimeter, thickness. It can be provided with tapered capillaries having a base in the plane of outer sheet 25 and an apex remote from the plane of outer sheet 25. The apices will, in general, lie in an imaginary plane remote from the plane of the outer sheet 25. These tapered capillaries will be provided with apex diameters, base diameters, angles of taper and heights as described and defined in the Thompson patent. FIG. 3 represents the cross sectional view of outer sheet 25 taken along the line 3—3 of FIG. 2 and assumes that outer sheet 25 of FIG. 2 is provided with such tapered capillaries. (FIGS. 1 and 2, of course, are generalized representations of diapers of this invention and are not limited to structures having tapered capillaries as defined here.) The tapered capillaries should have a base diameter of from about 0.013 to about 6.35 millimeters and an apex diameter of from about 0.0025 to about 2.54 millimeters. They should have a height of from about 0.025 to about 2.5 millimeters. The angle of taper should be greater than about 0° but less than about 90°. There should be from about 2 to about 1,400 tapered capillaries per square centimeter. Preferably the tapered capillaries will have base diameters, apex diameters, and heights in the range of, respectively, about 0.76 to about 1.27, about 0.25 to about 0.51, and about 0.25 to about 0.51 millimeters. Preferably, there should be from about 46 to about 132 tapered capillaries per square centimeter.

It was noted above that the elements described by Thompson are unidirectionally liquid impervious. That is to say, outer sheets provided with tapered capillaries will, in normal circumstances, permit liquid to flow in one direction only and not in the reverse direction. The liquid impervious direction is that from least diameter to greatest diameter of the tapered capillaries. This direction can be described alternatively by noting that when the bases of the tapered capillaries are in the plane of the sheet and the apices of the tapered capillaries are in an imaginary plane remote from the plane of the sheet, the fluid impervious direction is from the imaginary plane of the apices to the plane of the sheet.

Outer sheet 25 must be used in an orientation such that the direction of relative liquid impermeability is from the absorbent core to the exterior surface of the diaper. In the usual case, this means that the apices of the tapered capillaries in the outer sheet will be oriented in the direction of absorbent core and away from the exterior surface of the diaper.

Other materials, such as nonwoven sheets, can be used as the outer sheet so long as they meet the requirements delineated above.

Inner panel 24 can be constructed from any liquid impermeable material. Examples of such materials can be readily invisioned by those skilled in the art. The only requirements are that the materials be impermeable to liquid, flexible to such an extent that they do not interfere with the fit of the disposable diaper about the wearer, and of low bulk so that they do not appreciably add to the overall bulk of the disposable diaper thereby making it uncomfortable to wear. Naturally, the material should be innocuous to human skin and physically compatible with outer sheet 25 and absorbent core 23 and topsheet 22. One especially suitable material is polyethylene having a thickness of from about 0.013 to about 0.025 mm.

Figure 5:
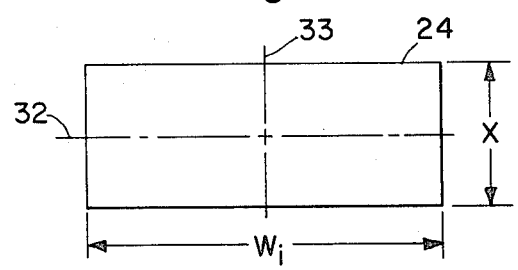
FIG. 5 is a representational plan view of the inner panel of this invention showing the various regions thereof.

Inner panel 24 is shown in representational plan view in FIG. 5. Center line 33 is an imaginary longitudinal center line while center line 32 is an imaginary latitudinal center line. The width of inner panel 24 is indicated generally by $W_i$ and its length by X. Crotch area 28 is shown in FIG. 5 merely to emphasize the fact that inner panel 24 is applied to the overall diaper in the crotch area. Reference letter X denotes the impervious region of inner panel 24. In the embodiment illustrated in FIG. 5 and FIG. 1, the length of the impervious area X is the total longitudinal length of inner panel 24.

Figure 6:
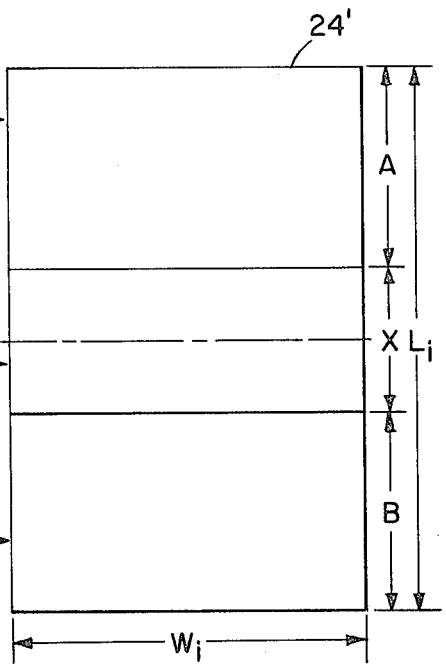
FIG. 6 is a representational plan view of another embodiment of the inner panel of this invention.

An alternate embodiment of the inner panel is shown in representational plan view as 24' in FIG. 6. Inner panel 24' is shown as a sheet having an impervious region X generally centered about imaginary lateral center line 32. Regions A and B extend laterally adjacent to and lie on either side of impermeable region X. Regions A and B must be essentially completely vapor permeable. That is to say, they must offer no practical resistance to vapor transfer therethrough. As a practical matter, materials which offer essentially no resistance to vapor transfer also freely permit the passage of liquids.

As in FIG. 1, in FIG. 6 reference numerals 26, 27, and 28 represent, respectively, front waist area, rear waist area, and crotch area. The general width of inner panel 24' is indicated by $W_i$, its length by $L_i$.

Inner panel 24' can be based on a tissue such as a high wet strength Kraft pulp paper tissue having a basis weight of, for example, 69.9 kilograms per 3,000 square meters. This tissue is treated in any suitable manner to render region X thereof impervious to liquid. For example, the tissue can be treated in region X with melted polyethylene or with a suitable wax is well known to those skilled in the art. The impevious region can also be formed by affixing a thermoplastic film to the tissue in the appropriate location. The only constraints placed upon the method in which the tissue is treated to render region X impervious are, in general, those restrictions placed on inner panel 24 as described above. That is to say, after treatment, region X must be impervious to liquids, must be flexible, must be no more bulky than appropriate for its intended use, must be innocuous to human skin, and must be compatible with the other elements of the disposable diaper. Preferably, the surface from which the tissue is treated is, in use, disposed away from the absorbent core.

Inner panel 24' as shown in FIG. 6 can be, and preferably is, an envelope tissue commonly used about absorbent core 23. In most disposable diapers which use an envelope tissue about the absorbent core, the envelope tissue generally faces the absorbent core on both its planar surfaces. It must be emphasized that in the practice of the present invention, when the envelope tissue is treated to provide inner panel 24', only the envelope tissue disposed toward the outer sheet is so treated.

Inner panel 24' can be a thermoplastic film wherein regions A and B are perforated in any convenient manner and region X is left unperforated.

Inner panel 24' can be, in fact, any material meeting the criteria mentioned above.

FIG. 2 is an exploded perspective view of an embodiment of the diaper of this invention in which inner panel 24' is a tissue wherein crotch area 28 has been treated to form impermeable region X as indicated. As before, regions 26, 27, and 28 are, respectively, the front waist area, the rear waist area, and the crotch area. Topsheet 22 is superimposed on absorbent pad 23. These two elements are then superimposed on inner panel 24' which, in turn, is superimposed on outer sheet 25. This stack of elements is then folded to form a diaper in the manner illustrated in FIG. 1.

As noted above, the reference letters in the figures represent relative dimensions. Reference letter $L_i$ denotes the longitudinal length of the inner panel 24' (i.e. the length in the direction from the front waist latitudinal edge to the rear waist longitudinal edge.) The longitudinal length of the impermeable region (which extends essentially across the entire lateral width of the diaper) is indicated by X. Preferably, X is from about 25% to about 85%, preferably about 65%, of the length of the absorbent core. $L_i$, when $L_i$ and X do not coincide, is of any convenient length depending on the length of the absorbent core. The lengths A and B are then selected for convenience with the only restraint being that the impermeable area must fall within the crotch region of the diaper. (As used herein, the length of the absorbent core is the longitudinal dimension of the absorbent core and corresponds to the longitudinal dimension of the outer sheet as defined above.) Regions A and B can be folded about the absorbent core.

In a similar vein, referring to FIG. 4, the vapor pervious, relatively liquid impervious region of outer sheet 25 extends longitudinally essentially the entire length of outer sheet 25. The lateral width of this central vapor pervious, relatively impervious region is designated by Z. The impermeable regions of outer sheet 25 likewise extend essentially the entire longitudinal length of the outer sheet 25 and have widths, respectively, C and D. Impermeable regions C and D essentially provide the free side flap leg seal for the diaper. In general, C and D are each greater than about 5 centimeters, preferably each is about 7.6 centimeters.

The lateral widths $W_i$ of the inner panel and $W_o$ of the outer sheet are convenient dimensions. Preferably, the outer sheet is at least about 10 centimeters wider than the inner panel. The inner panel is normally substantially the same width as the absorbent core.

Normally, disposable diapers are used for diapering infants. In this normal situation, the longitudinal length $L_O$ of outer sheet 25 is from about 30 to about 52 centimeters while the longitudinal length $L_i$ of the inner sheet 24' is from about 38 to about 53 centimeters. Preferably, the width $W_i$ of inner panel 24 is from about 21 to about 34 centimeters and the width $W_O$ of outer sheet 25 is from about 31 to about 43 centimeters. The absorbent core is generally from about 26 to about 45 centimeters in the longitudinal direction and from about 21 to about 34 centimeters in lateral width.

Disposable diapers can, however, be sized to fit adult humans. In fact, there is a great commercial demand for adult-sized disposable diapers for use with incontinent human adults. When intended for use by adults, $L_O$ is preferably from about 71 to about 102 centimeters while $L_i$ is from about 76 to about 110 centimeters. Preferably, the inner panel is from about 30 to about 54 centimeters wide and the outer sheet is from about 45 to about 79 centimeters wide. Absorbent pads are, then, about 58 to about 87 centimeters in the longitudinal direction and about 30 to about 54 centimeters in lateral width. As before, X is from about 25% to about 85%, preferably about 65%, of the length of the absorbent core.

As indicated above, inner panels 24 and 24', outer sheet 25, and the entire disposable diaper 21 are all represented in the drawings as rectangular devices. These rectangular devices are essentially as described in U.S. Pat. No. Re. 26,151. U.S. Pat. No. 3,860,003 teaches disposable diapers having unfolded configurations somewhat different from the rectangular configuration shown in the drawings. It is to be understood that the present invention can be readily adapted to configurations such as that taught by U.S. Pat. No. 3,860,003. In such circumstances the absolute dimensions of $L_O$ and $L_i$ and absorbent core length and width will vary according to need. The various regions of inner panel 24 and 24' and outer sheet 25 will retain their relative dimensional relationships, but the absolute width and length of these regions will vary.

The inner panel and the outer sheet can be associated in any of various ways. In a preferred embodiment, the two elements are not affixed to one another except, perhaps, at the folded lateral margins of the diaper. That is to say, the inner panel is merely placed adjacent the outer sheet between it and the absorbent core; they are not united one to another in any way.

In another preferred embodiment, the inner panel is affixed to the outer sheet by adhesive beads or spots. For example, multiple narrow beads of adhesive extending parallel to the imaginary longitudinal centerline and extending essentially over the whole length of the impervious portion of inner panel 24 can be used to unite these two elements. These multiple beads can be spaced from about 0.6 to about 5 centimeters apart. Beads of adhesive applied in this particular orientation serve not only to unite the inner panel and the outer sheet, but also to restrict lateral migration of any liquid which may inadvertently migrate into the region between the inner panel and the outer sheet. Prevention of such lateral migration of liquid serves to ensure that there is no leakage of liquid from the lateral edges of the diaper when used, as about the wearer's legs. Preferably, a longitudinal bead of adhesive is applied to the diaper the side flap region for the same reason even in the absence of other beads of adhesive in the diaper. Any adhesive, such as hot melt adhesive, well known to those skilled in the art can be used.

In another embodiment, the inner panel can be adhesively affixed to the outer sheet along each laterally extending edge of the impervious portion of the inner panel. That is to say, the inner panel can be affixed to the outer sheet by adhesive extending across the width of the diaper on either edge of the impervious portion of the inner panel. Hot melt adhesive can be used as can adhesive tape having adhesive applied to both planar surfaces of the tape.

In order to better illustrate the invention, and not by way of limitation, the following examples are presented.

EXAMPLES

To demonstrate the present invention, and not by way of limitation, the following examples are presented.

Disposable diapers similar in form, size, and construction to a leading commercially available diaper and of the design illustrated generally by FIG. 1 were constructed.

Sample A

The absorbent core was formed of airlaid, comminution grade wood pulp, had a basis weight of 0.028 gram per square centimeter, and was approximately 40.6 centimeters in longitudinal length by 30.2 centimeters and lateral width. The absorbent core was covered on the face nearest the topsheet with a paper tissue having a basis weight of 57.9 kilograms per 3000 square meters. A topsheet of spunbonded polyester fibers, having a basis weight of about 23.5 grams per square meter, and being about 30.2 centimeters by about 47 centimeters was superimposed over one face of the absorbent core. The outer sheet was 0.025 millimeter polyethylene provided with tapered capillaries having a base diameter of 0.813 millimeter, an apex diameter of 0.279 millimeter, and a height of 0.401 millimeter. There were 128 tapered capillaries per square centimeter. The outer sheet was 48.3 centimeters ($L_O$) by 38.1 centimeters ($W_O$). It had an R value of 11.4. The inner panel was a paper tissue of 69.9 kilograms per 3000 square meters basis weight and was 47 centimeters ($L_i$) by 30.2 centimeters ($W_i$). The impervious region was obtained by coating the central portion of the tissue with melted polyethylene so the dimension X was 26.7 centimeters. This inner panel was placed adjacent the outer sheet between it and the absorbent core as shown generally in FIG. 2. The backsheet comprising the outer sheet and inner panel was superimposed on the absorbent core-topsheet assembly and the total unit was folded into a disposable diaper generally as shown by FIG. 1. A hot melt adhesive bead was placed longitudinally along each side flap region. It should be emphasized that the only points of direct attachment between the outer sheet and the inner panel were in the folded side flap areas of the diaper.

Sample B

Sample B was prepared as Sample A, except the inner panel was an impervious polyethylene film which was 30.2 centimeters ($W_i$) by 26.7 centimeters (X). It was adhesively fastened to the outer sheet with double sided adhesive tape along its laterally extending edges. The absorbent pad was faced on its backsheet side with the 69.9 kilograms per 3000 square meters tissue as before, but this tissue lacked an impervious region.

Sample C

Sample C was the control sample and represented a conventional disposable diaper. It was constructed as Sample B, except there was no inner panel. The outer sheet was impermeable polyethylene of 0.025 millimeter thickness, thereby representing a conventional disposable diaper back-sheet.

To determine the amount of vapor which will evaporate from the disposable diaper of this invention as it is worn (and thereby measure and demonstrate the breathability of the two element backsheet of this invention), the following tests were conducted.

The sample was folded into the normal disposable diaper configuration as if it were to be affixed to an infant. That is to say, the front and rear waist areas were brought into close proximity one to another thereby folding the diaper into a U shape. The topsheet formed the inner surface of the U; the backsheet, either the two element backsheet of this invention or the conventional control backsheet, formed the outer surface of the U. In Samples A and B the inner panel was generally at the bottom of the U. An aliquot of synthetic urine was added to the crotch region of each diaper to simulate soiling. The aliquot was either 70 milliliters to simulate daytime usage or 150 milliliters to simulate nighttime usage. The wetted diapers were sealed along all open edges with double sided adhesive tape to simulate the closure of the diaper about the legs and waist of an infant.

The samples were subjected to static and dynamic evaporation (breathability) tests.

For the static test, a diaper, prepared as indicated, was suspended with the waist regions uppermost and the crotch region freely hanging downwardly. The sample was placed in a 23° C., 50% relative humidity atmosphere for two hours. The weight loss occuring during this time was observed and recorded and reported as weight % of initial loading evaporated.

For the dynamic test, the diapers were prepared and suspended as for the static test. In this case, however, the diapers were manipulated to simulate an infant's movement. The manipulation was provided by a simple motorized mechanical device which pressed againt the crotch region of the suspended diaper and alternately raised the crotch region through a distance of approximately 7.6 centimeters upwardly toward the fixed waist region and then lowered the crotch region to its original position at a rate of approximately 15 cycles per minute. Observations were made and data recorded as for the static test.

Five units of each diaper sample were tested and the average results for the static test are shown in Table I, for the dynamic test in Table II.

TABLE I

| STATIC TEST | | | |
| --- | --- | --- | --- |
| Daytime Use | | Nighttime Use | |
| Sample | % Evaporation | Sample | % Evaporation |
| A | 0.64 | A | 1.65 |
| B | 0.47 | B | 1.35 |
| C | 0.07 | C | 0.36 |

TABLE II

| DYNAMIC TEST | | | |
| --- | --- | --- | --- |
| Daytime Use | | Nighttime Use | |
| Sample | % Evaporation | Sample | % Evaporation |
| A | 1.78 | A | 2.29 |
| B | 1.59 | B | 1.88 |
| C | 0.45 | C | 0.45 |

As can be readily observed, the diapers of this invention allowed more liquid to evaporate than did conventional disposable diapers. Thus, the diapers of this invention breathe more effectively than do conventional disposable diapers. Sample A, wherein the inner panel is not affixed to the outer sheet other than in the folded side flap areas at the longitudinal edges of the diaper, was shown to be more effective than another embodiment.

At the same time the evaporation (breathability) tests were being conducted, careful observations were made to determine if any liquid was present on the outer surface of the diapers. Essentially no liquid was observed on the outer surfaces of any of the samples.

Diapers are constructed as Sample B, except the inner panel is omitted entirely. These diapers demonstrate adequate evaporation or breathability, but at the same time allow excessive quantities of liquid to pass through the outer sheet. Therefore, these samples are unsuitable for practical use because adjacent clothing is soiled.

Diapers corresponding to Samples A, B, and C are prepared and are evaluated by use on living infants. The mothers of the infants judge all samples to provide adequate protection from the wetting or soiling of outer garments and judge the diapers of this invention to be drier overall and cooler than conventional disposable diapers.

The foregoing detailed description of the invention has been couched in terms of disposable diapers. It is anticipated that this invention, comprising an absorbent core and a breathable backsheet of specific configuration, can be used in other embodiments. For example, the absorptive device of this invention can be shaped and sized for use as a surgical bandage and as a sanitary napkin. The details of the extension of the teachings of this invention to such embodiments are well within the skills of the ordinary artisan.

What is claimed is:

1. A disposable diaper comprising an absorbent core; a vapor pervious, relatively liquid impervious outer sheet; and a liquid impervious inner panel; wherein said inner panel is substantially as wide as said absorbent core and is from about 25% to about 85% of the length of said absorbent core; wherein said inner panel is superimposed on said outer sheet to form a breathable backsheet and said absorbent core is superimposed on said backsheet in such a manner that said inner panel is interposed between said absorbent core and said outer sheet and is located in the crotch region of said diaper.

2. The diaper of claim 1 wherein said outer sheet has a liquid transfer rate of less than about 5% and a vapor transfer rate greater than about 0.6 gram per 100 square centimeters per hour.

3. The diaper of claim 2 wherein said outer sheet is impermeable along the lateral margins thereof.

4. The diaper of claim 1 wherein said outer sheet is impermeable along the lateral margins thereof.

5. The diaper of claim 1, 2, 3 or 4 wherein said outer sheet is constructed of an impermeable film having perforations therethrough whereby the R value of the vapor permeable, relatively liquid impervious region of said film is from about 2 to about 40.

6. The diaper of claim 5 wherein said R value is from about 5 to about 25.

7. The diaper of claim 1, 2, 3, or 4 wherein said outer sheet is constructed of an impermeable film provided with tapered capillaries having a base in the plane of said film and an apex remote from said film; wherein the diameter of said apex is from about 0.0025 to about 2.54 millimeters; the diameter of said base is from about 0.013 to about 6.35 millimeters; the height of said capillaries is from about 0.025 to about 1.02 millimeters; and the angle of taper of said capillaries is greater than about 0° C. and less than about 90° C.; and wherein there are from about 2 to about 1,400 tapered capillaries per square centimeter.

8. The diaper of claim 7 wherein the base diameter of said tapered capillaries is from about 0.76 to about 1.27 millimeters, the apex diameter is from about 0.250 to about 0.51 milimeter; the height is from about 0.010 to about 0.020 millimeter; and there are from about 46 to about 132 tapered capillaries per square centimeter.

9. The diaper of claims 1, 2, 3, or 4 wherein said inner panel is constructed from a sheet provided with an impermeable region and at least one essentially completely vapor permeable region, wherein said impermeable region is substantially as wide as said absorbent core and is from about 25% to about 85% of the length said absorbent core.

10. The diaper of claim 5 wherein said inner panel is constructed from a sheet provided with an impermeable region and at least one essentially completely vapor permeable region, wherein said impermeable region is substantially as wide as said absorbent core and is from about 25% to about 85% of the length said absorbent core.

11. The diaper of claim 6 wherein said inner panel is constructed from a sheet provided with an impermeable region and at least one essentially completely vapor permeable region, wherein said impermeable region is substantially as wide as said absorbent core and is from about 25% to about 85% of the length said absorbent core.

12. The diaper of claim 7 wherein said inner panel is constructed from a sheet provided with an impermeable region and at least one essentially completely vapor permeable region, wherein said impermeable region is substantially as wide as said absorbent core and is from about 25% to about 85% of the length said absorbent core.

13. The diaper of claim 8 wherein said inner panel is constructed from a sheet provided with an impermeable region and at least one essentially completely vapor permeable region, wherein said impermeable region is substantially as wide as said absorbent core and is from about 25% to about 85% of the length said absorbent core.

14. A disposable diaper comprising (a) an absorbent core comprising air laid comminuted wood pulp fibers and having a basis weight of about 0.03 gram per square centimeter;

(b) a vapor pervious, relative liquid impervious outer sheet comprising a polyethylene film of about 0.025 millimeter thickness provided with about 130 tapered capillaries per square centimeter, said tapered capillaries having a base of about 0.81 millimeter diameter in the plane of said film and an apex of about 0.28 millimeter diameter in a plane remote from the plane of said film and a height of about 0.40 millimeter; and (c) an inner panel comprising a paper tissue having a basis weight of about 70 kilograms per 3000 square meters provided with an impermeable region substantially as wide as said absorbent core and about 65% of the length of said absorbent core;

wherein said inner panel is superimposed on said outer sheet to form a breathable backsheet and said absorbent core is superimposed on said backsheet in such a manner that said inner panel is interposed between said absorbent core and said outer sheet and said impermeable region is located in the crotch region of said diaper.

15. The diaper of claim 14 wherein said impermeable region comprises a thermoplastic film.

16. The diaper of claim 14 wherein said impermeable region comprises paper fibers coated with thermoplastic polymers.

17. The diaper of claims 14, 15, or 16 comprising as an additional element a fluid pervious topsheet.

* * * * *

UNITED STATES PATENT AND TRADEMARK OFFICE
CERTIFICATE OF CORRECTION

PATENT NO. : 4,341,216
DATED : July 27, 1982
INVENTOR(S) : MARY C. OBENOUR

It is certified that error appears in the above-identified patent and that said Letters Patent are hereby corrected as shown below:

In Claim 8, Column 12 at line 29:

delete "0.010" and insert therefor --0.25--

Column 12 at line 30:

delete "0.020" and insert therefor --0.51--

Signed and Sealed this

Second Day of August 1983

[SEAL]

Attest:

Attesting Officer

GERALD J. MOSSINGHOFF

Commissioner of Patents and Trademarks